(12) United States Patent
Pan et al.

(10) Patent No.: US 6,770,758 B2
(45) Date of Patent: Aug. 3, 2004

(54) POLYSACCHARIDE SEPARATION METHOD

(75) Inventors: Li-Chun Pan, Hsinchu (TW); Chih-Ching Chien, Hsinchu (TW); Chun-Min Chang, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 10/639,477

(22) Filed: Aug. 13, 2003

(65) Prior Publication Data

US 2004/0127701 A1 Jul. 1, 2004

(30) Foreign Application Priority Data

Dec. 27, 2002 (TW) ........................................ 91137654 A

(51) Int. Cl.[7] .............................. C07H 1/06; C07H 1/00; C07K 14/42
(52) U.S. Cl. .................... 536/127; 536/124; 536/123.1; 536/123.12; 530/396
(58) Field of Search ................. 536/127, 124, 536/123.1, 123.12; 530/396

(56) References Cited

U.S. PATENT DOCUMENTS 5,998,588 A    12/1999  Hoffman et al.
6,258,275 B1 *  7/2001  Freitag et al. .............. 210/632

OTHER PUBLICATIONS

Pan, Li–Chun, et al., A novel application of thermo—responsive polymer to affinity precipitation of polysaccharide, Journal of Biochemical and Biophysical Methods, Methods 55, 2003, pp. 87–94.

* cited by examiner

*Primary Examiner*—Samuel Barts
*Assistant Examiner*—Michael C. Henry
(74) *Attorney, Agent, or Firm*—Sughrue Mion, PLLC

(57) ABSTRACT

A method for the separation of polysaccharides. The method comprises conjugating a ligand to a thermo-sensitive polymer to form a conjugate, wherein the ligand specifically recognizes a polysaccharide, and the thermo-sensitive polymer features a lower critical solution temperature (LCST), contacting a mixture containing a desired polysaccharide with the conjugate at an environmental temperature lower than the LCST to form a polysaccharide-conjugate complex, collecting the polysaccharide-conjugate complex at an environmental temperature higher than the LCST, and releasing the polysaccharide from the polysaccharide-conjugate complex to obtain the desired polysaccharide.

17 Claims, 3 Drawing Sheets

POLYSACCHARIDE SEPARATION METHOD

BACKGROUND OF THE INVENTION

1. Field of the Invention

The present invention relates to a method for the separation of polysaccharides. More particularly, the present invention relates to a method for the separation of polysaccharides using conjugates of thermo-sensitive polymers and ligands.

2. Description of the Related Arts

Carbohydrate-containing molecules play important roles in many aspects of-human physiological responses, including the modulation of the immune system and exertion of tumor-inhibitory effects. At the molecular level, cell-cell recognition as well as signal transduction has been noted to involve carbohydrate-protein interactions.

In addition to their role as nutrient for energy production, carbohydrate-containing molecules are also believed to participate in important regulatory and functional roles in metabolism. Moreover, some polysaccharides are considered as immunonutrients; for example, compounds extracted from several mushrooms, in particular (1→3)-β-D-glucans, show the ability to modulate the immune system as well as anti-inflammatory responses and exhibit potential antitumor activity (Borchers AT, et al. Mushrooms, tumors, and immunity. Proc Soc Exp Biol Med, 1999, 221:281–93). Polysaccharides prepared from many species of fungi such as *Cordyceps sinensis* and *Ganoderma lucidum* (Ling Zhi mushroom) are now widely used as health food supplements in Asia and have been shown to provide effects beneficial to general health; however, the mechanisms involved are poorly understood. An understanding of the molecular mechanisms involved requires an effective separation method, providing sufficient purity while preserving activity.

To elucidate the mechanisms of these glycoproteins involved in the various biological processes, one needs to embark on an arduous task of first separating the polysaccharide in reasonably purity from their indigenous biological mixtures. In general, it is necessary to conduct these separations at a temperature which does not inhibit biological activity due to heat denaturation. Lastly, the chemical heterogeneity of the polysaccharides involved may complicate the understanding of the underlying mechanisms. Because of these factors, the study of glycobiology has fallen behind those of nucleotides and proteins.

"Intelligent (smart) polymers", or so called "stimuli-responsive polymers" or "environmentally sensitive polymers", show distinct property changes to small changes in environmental conditions, such as solution pH, ionic strength, solvent composition, temperature, light, and electric field. These polymers have applied in medicine and biotechnology. A few examples are cell and protein attachment/detachment used in therapeutic devices, bioactive surfaces for enzyme immobilization, drug delivery and affinity separation (Hoffman AS, et al. Conjugation of stimuli-responsive polymers and biomolecules: random and site-specific conjugates of temperature-sensitive polymers and proteins. Macromol Symp, 1997; 118:553–563).

Purification using these polymers on biomolecules usually involves the attachment of biotin to polymers such as poly(N-isopropylacrylamide). This conjugate is then used to separate streptavidin-containing mixtures, as in U.S. Pat. No. 5,998,588. As best as we know, there have not been any efforts in attaching affinity ligands to these polymer networks for the purification of polysaccharides and related compounds.

SUMMARY OF THE INVENTION

It is therefore a primary object of the present invention to develop a rapid, technically simple and cost effective method for the purification/partial purification of bioactive polysaccharides by introducing a smart polymer in the affinity purification.

The method for the separation of polysaccharides in the invention comprises conjugating a ligand to a thermo-sensitive polymer to form a conjugate, wherein the ligand specifically recognizes a polysaccharide, and the thermo-sensitive polymer features a lower critical solution temperature (LCST), contacting a mixture containing a desired polysaccharide with the conjugate at an environmental temperature lower than LCST to form a polysaccharide-conjugate complex, collecting the polysaccharide-conjugate complex at an environmental temperature higher than LCST, and releasing the polysaccharide from the polysaccharide-conjugate complex to obtain the desired polysaccharide.

BRIEF DESCRIPTION OF THE DRAWINGS

The present invention will be more fully understood and further advantages will become apparent when reference is made to the following description of the invention and the accompanying drawings in which:

In FIG. 2A, X axis represents ConA uptake (mg) and Y axis represents time (hours); in FIG. 2B, X axis represents ConA uptake (mg) and Y axis represents ConA concentration (mg/ml).

DETAILED DESCRIPTION OF THE INVENTION

Figure 1:
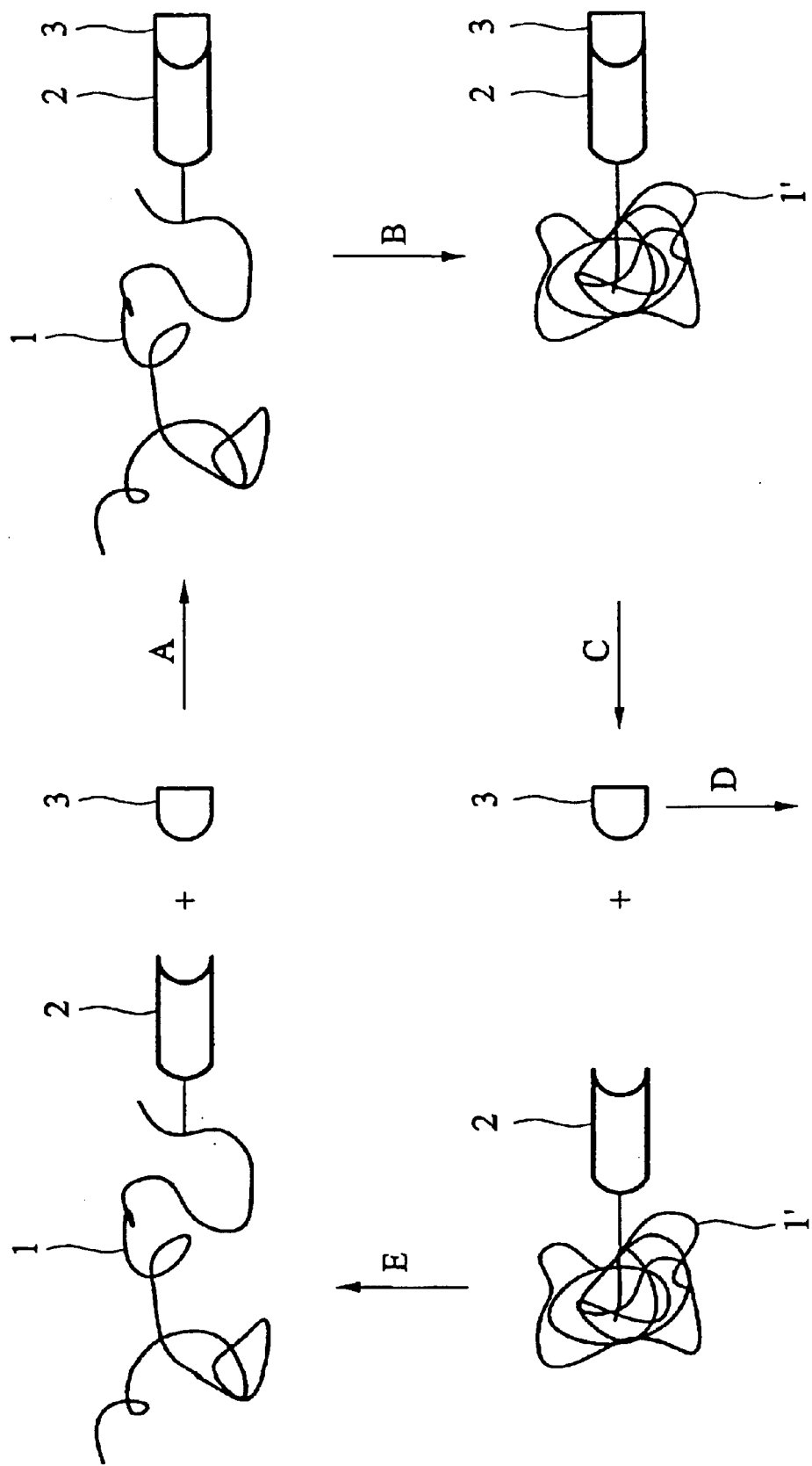
FIG. 1 is a diagram illustrating the process of the present invention.

Without intending to limit it in any manner, the present invention will be further illustrated by the following description.

The present invention features a method for the separation of polysaccharides. The method comprises conjugating a ligand to a thermo-sensitive polymer to form a conjugate, wherein the ligand specifically recognizes a polysaccharide, and the thermo-sensitive polymer features a lower critical solution temperature (LCST), contacting a mixture containing a desired polysaccharide with the conjugate at an environmental temperature lower than LCST to form a polysaccharide-conjugate complex, collecting the polysaccharide-conjugate complex at an environmental temperature higher than LCST, and releasing the polysaccharide from the polysaccharide-conjugate complex to obtain the desired polysaccharide.

The thermo-sensitive polymers useful to make the conjugates described herein can be any which are sensitive to temperature that cause significant conformational changes in the polymer coil, and which can be engineered to contain group which is reactive with specific groups on the interactive molecules (e.g., ligands). The thermo-sensitive polymer used herein can include, but is not limited to, poly(N-isopropylacrylamide) PNIPAAm), poly(vinylmethylether), or poly(vinylmethyloxazolidone) In one preferred embodiment, PNIPAAm is applied.

PNIPAAm is a thermally sensitive polymer that precipitates out water at 32° C., which is its lower critical solution temperature (LCST) (Chen G. et al. Bioconjug Chem, 1993; 4:509–513; Chen G, et al. J Biomater Sci Polym Ed, 1994;

5:371–382; Hoshino K, et al. Biotechnol Bioeng, 1998; 60:568–579). That is, the polymer becomes insoluble and phase separation occurs when the temperature rises above 32° C., and becomes soluble in the aqueous phase once the temperature drops below the LCST. Therefore, polysaccharides conjugated with the thermo-sensitive polymer can be separated by simply changing temperature.

The ligand used herein includes any molecule capable of a specific binding interaction with polysaccharides. The ligand used herein is the lectin. Lectins are non-enzymatic, carbohydrate binding proteins that specifically recognize diverse sugar structures (Vijayan M, et al. Curr Opin Struct Biol 1999; 9:707–714). Examples of lectins include, but are not limited to, concanavalin A (ConA), lentil lectin, or wheat germ lectin (WGL). In preferred embodiments, ConA or WGL can be applied. Among the commercially available immobilized lectins, ConA and WGL are the most commonly used. ConA specifically binds to the molecules that contain α-D-mannosyl and α-D-glucosyl residues while WGL binds N-acetyl-β-glucosaminyl residue (Van Landschoot A, et al. Eur J Biochem 1980; 103:307–312). Substrates bonded to the immobilized lectin may be displaced by a high concentration of a competitive substrate or by a salt. The competitive substrate can include, but is not limited to, α-glucopyroside, α-mannopyroside, or N-acetylglucosamine, and the salt can include, but is not limited to, sodium borate.

In one preferred embodiment of the invention, the thermo-sensitive polymer PNIPAAm and ConA can be conjugated as:

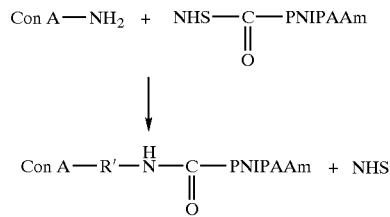

The NHS ester is known to be very reactive towards amino groups and has been widely used as a functional group for coupling reactions with protein (Chen G, et al. Bioconjug Chem 1993; 4:509–514). Thus, the NHS-activated end group on the polymer has been coupled with the amino group of the lectin receptor via formation of a peptide bond. The result was a thermo-responsive, phase separating polymer-lectin receptor conjugate (PNIPAAm-ConA) with the NHS as the leaving group. The coupling efficiency of ConA to PNIPAAm is at least 44%, and of WGL 5.1%.

The mixture containing desired polysaccharides of the invention can be from plants or fungi, including *Bupleurum falcatum, Ganoderma lucidum, Cordyceps sinensis*, or saccharomycetes. In one preferred embodiment, the mixture contains β-glucan.

In addition, in the separation method of the present invention, release of the polysaccharide is accomplished by replacing the polysaccharide of the conjugate with a competitive substrate. The competitive substrate can include, but is not limited to, α-glucopyroside, α-mannopyroside, or sodium borate.

Moreover, in the separation method of the present invention, an additional step after polysaccharide release comprises recovering the conjugate at an environmental temperature lower than the LCST.

In another preferred embodiment, the separation method of the present invention further comprises repeating the contacting, collecting, and release steps to obtain a high production of the polysaccharide.

In the separation method of the present invention, an additional purification step can be performed to the polysaccharide obtained. The purification can include ion-exchange or gel filtration.

FIG. 1 shows the process of the separation method of the present invention. Thermo-sensitive polymer 1 is conjugated with ligand 2 to obtain a conjugate, and the conjugate is contacted with bioactive polysaccharide 3 to specifically bind bioactive polysaccharide 3 to thermo-sensitive polymer 1 via ligand 2. The environmental temperature is then raised to higher than the LCST of thermo-sensitive polymer 1. Thermo-sensitive polymer 1 bound to bioactive polysaccharide 3 via ligand 2 is precipitated and the precipitate is collected. After that, polysaccharide 3 can be released from the conjugate by a competitive substrate. Bioactive polysaccharide 3 can be further purified as needed. Finally, the temperature is reversed to recover thermo-sensitive polymer 1 and ligand 2.

Practical examples are described herein.

EXAMPLE 1

Synthesis of Thermo-sensitive Hydrogel Polymer

N-isopropylacrylamide (NIPAAm) monomer and N,N'-azobisisobutyronitrile (AIBN) were purchased from Aldrich Co. (Milwaukee, Wis., USA), N,N'-dicyclohexylcarbodiimide (DCC) and 3-mercaptopropionic acid (MPA) were purchased from ACROS Organics (Geel, Belgium), N-hydroxy-succinimide (NHS) was obtained from Fluka (Switzerland), N,N'-dimethylformide (DMF), dichloromethane and ether were purchased from TEDIA (Fairfield, Ohio, USA). All chemicals were reagent grade and subjected to use for the synthesis of the thermo-sensitive hydrogel polymer.

PNIPAAm was prepared as described previously with slight modifications (Takei YG, et al. Bioconjug Chem 1993; 4:42–46; Park TG, et al. J Biomater Sci Polym Ed; 4: 493–504; and Mattiasson B, et al. J Mol Recognit 1998; 11:211–216). In short, 5 g of NIPAAm was added into 35 g of DMF and stirred slowly until completely dissolved. Then, 0.11 g of MPA was added to the mixture. The temperature was increased to 70° C. and 0.04 g of AIBN was then added to the reaction mixture and incubated for 5 h. The polymer was then purified by repeated precipitation with diethyl ether.

N-hydroxysuccinimide esterified PNIPAAm was first prepared by dissolving PNIPAAm (4 g) into 40 ml dichloromethane with DCC (2 mmol) under stirring in an ice bath for 30 min. NHS (2 mmol) was then added into the reactant slowly and incubated for 4 h. The reactant was then concentrated and the product purified by repeated precipitation with diethyl ether.

PNIPAAm was synthesized by radical polymerization using AIBN and MPA as initiators and chain-transfer reagents, respectively. NHS-esterified PNIPAAm was prepared by esterification of carboxylated PNIPAAm with N-hydroxysuccinimide in dichloromethane in the presence of DCC to obtain a functionally reactive NHS group at one end of the polymer. The chemical structure of PNIPAAm was identified by $H^1$-NMR using d-chloroform as solvent. The polymer has an average molecular weight of 4244 as determined by gel permeation chromatography. The lower critical separation temperature (LCST) of the polymer was about 32° C. as determined by Differential Scanning Calorimetry (DSC).

EXAMPLE 2

Conjugation of Lectin Receptor to Thermo-responsive Hydrogel Polymer 20 mg of NHS-esterified PNIPAAm was dissolved in a pH 7.4 coupling buffer containing 20 mM Tris-HCl, 0.5 M NaCl, 1 mM $MnCl_2$ and 1 mM $CaCl_2$ and either ConA (1 mg/ml) or WGL (1 mg/ml) ($MnCl_2$ and $CaCl_2$ were omitted in the buffer when WGL was used as ligand). The reaction mixture was held at 4° C. for 2 h to allow the peptide bond formation and then warmed to 37° C. in order to precipitate the PNIPAAm-lectin conjugate. The resulting precipitate was recovered by centrifugation at 37° C. with a Personal Microcentrifuge (6400 rpm; 2000×g; USA Scientific, Inc, Ocala, Fla., USA) inside an oven. The precipitate was washed with coupling buffer and recovered by centrifugation. Coomassie blue was used to determine the protein amount left in the solution. The amount of lectin conjugated by PNIPAAm can then be calculated indirectly from the difference in protein totals before and after precipitation in the supernatant. The coupling efficiency was calculated as:

Coupling efficiency (%)=actual binding number/theoretical binding number×100

The resulting precipitate was then dissolved in a cold binding buffer and the solution was used as a thermo-responsive adsorbent for polysaccharides and stored at 4° C. for further use.

Figure 2A:
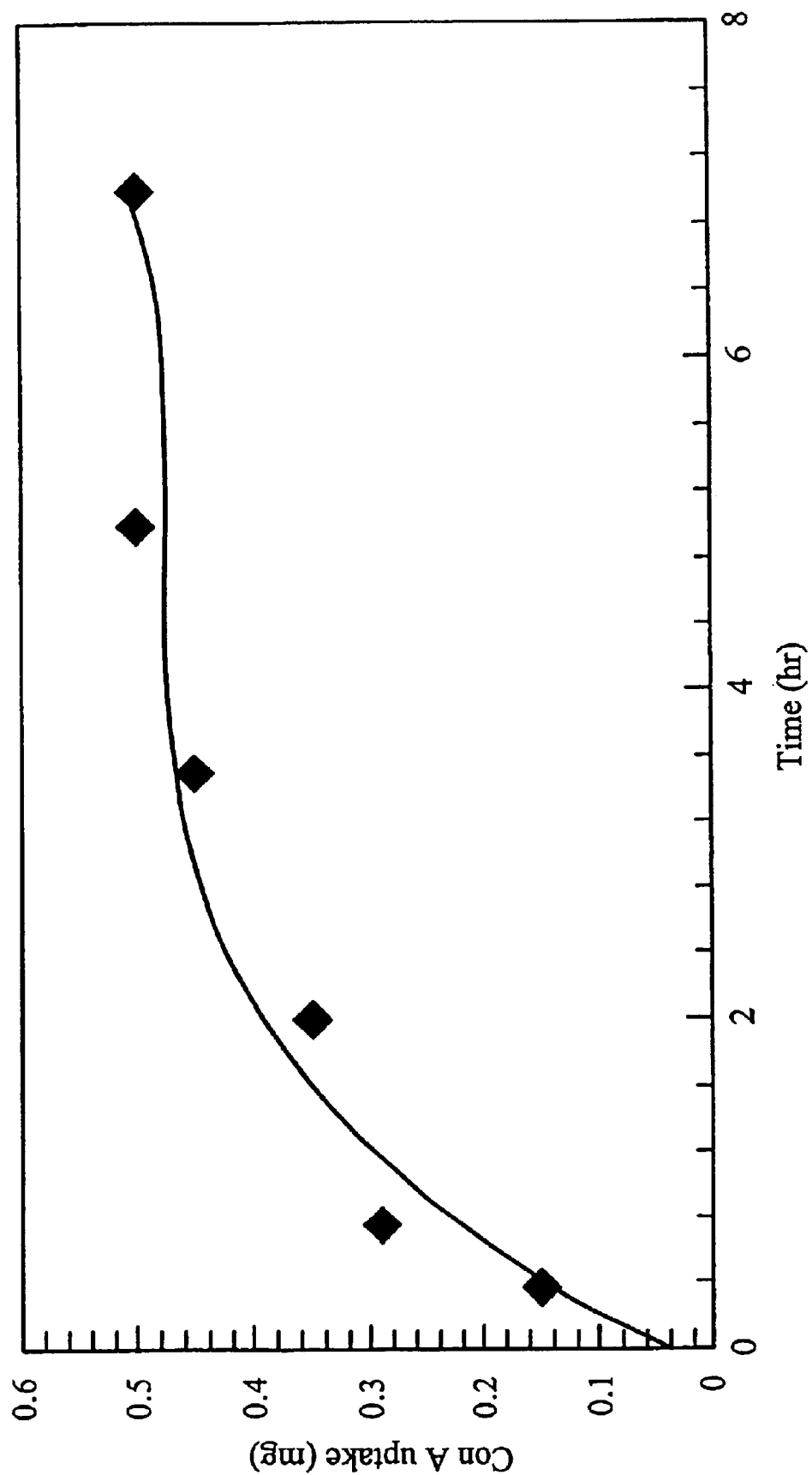
FIG. 2A–2B are diagrams showing ConA uptake efficiency using PNIPAAm as the affinity ligand in the invention.
Figure 2B:
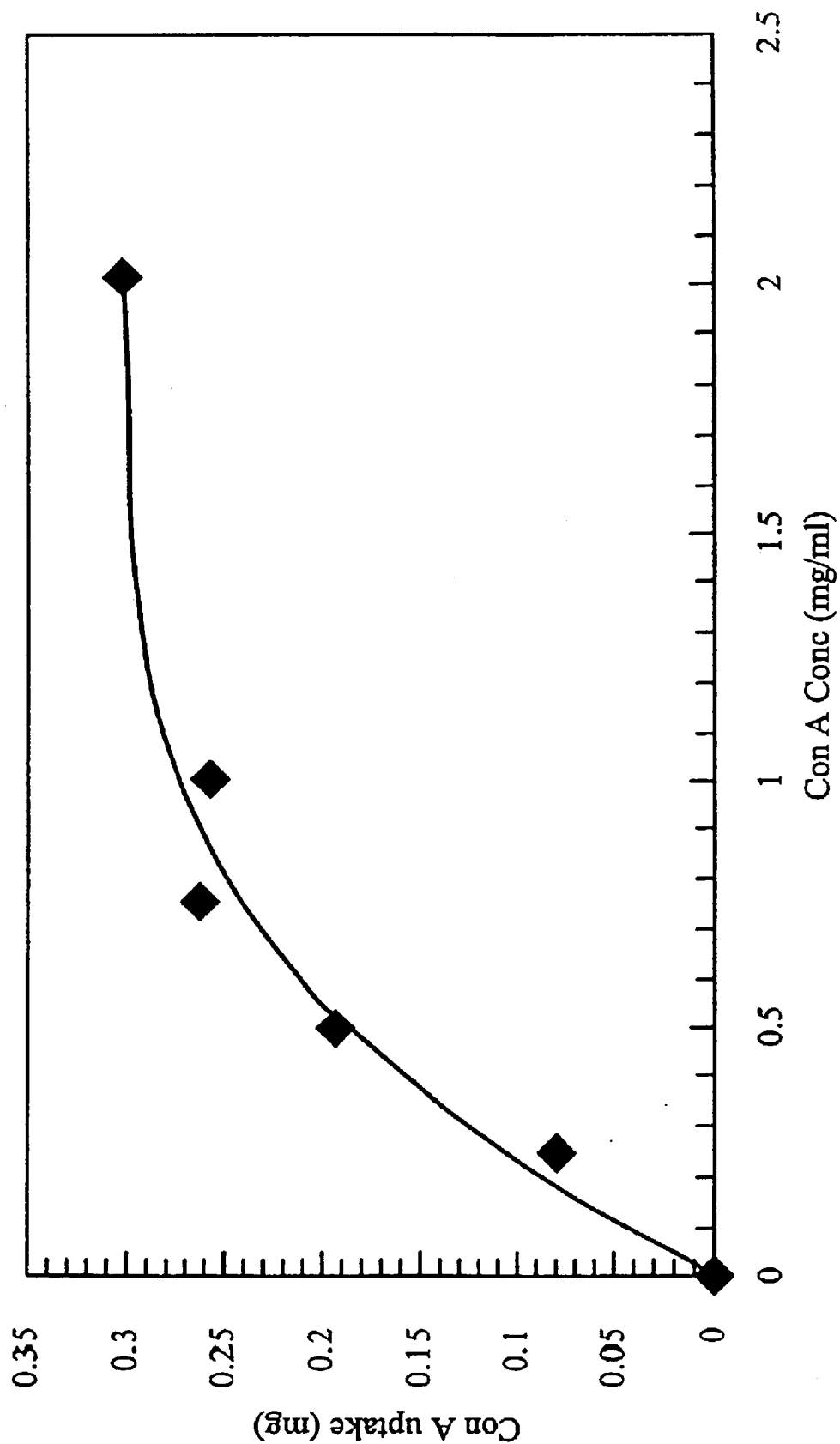

The adsorption efficiencies of ConA or WGL as affinity ligands to the thermo-responsive polymer PNIPAAm were also evaluated at 4° C., pH 8.3. FIG. 2A shows the adsorption capacity of PNIPAAm to ConA determined as a function of time. The amount of ConA uptake by PNIPAAm reached its maximum (13 mg ConA/g polymer) after 4 h incubation (FIG. 2A). The minimal concentration of ConA in the reaction mixture to achieve optimal coupling efficiency was also evaluated and found to be 1 mg/ml (FIG. 2B). In addition, different buffering systems with various pH values (for example, phosphate-based buffering system-with pH 7.4) were evaluated for their binding capacity, and the results show that carbonate-based buffering system is preferred.

EXAMPLE 3

Separation and Recovery of Polysaccharide Compounds from Reaction Mixture by Affinity Precipitation A mixture of biomolecules containing β-1,3 glucan (poly-(1,6)-β-D-glucopyranosyl-(1,3)-β-D-glucopyranose), BSA and DNA was used to evaluate the binding affinity of the thermo-responsive adsorbent. β-1,3 glucan was purified from baker yeast as described by Jamas et al (U.S. Pat. No. 5,322,841). Thermo-responsive adsorbent (about 10 mg of adsorbent) and the biomolecule mixture (containing 1 mg/ml of β-1,3 glucan or, 0.5 mg BSA and DNA) were mixed thoroughly in pH 7.4 binding buffer (20 mM Tris-HCl, 0.5 M NaCl, 1 mM $MnCl_2$, 1 mM $CaCl_2$). The reaction mixture was incubated at 4° C. with slow stirring for 1 h, and the temperature was raised to 37° C. and the precipitate (adsorbent with target biomolecule) formed was separated by centrifugation with a Personal Microcentrifuge (6400 rpm; 2000×g). The precipitate was washed in cold binding buffer and re-precipitated twice as described above.

Methyl α-D-mannopyranoside (0.1 M) or N-acetylglucosamine (0.1 M) were used as desorption reagents to desorb polysaccharides or glycoproteins from the adsorbent when ConA or WGL was used as ligand, respectively. These compounds have higher affinity toward ConA/WGL than β-1,3 glucan/Ovomucoid and thus can displace the bound ConA/WGL.

The results are shown in Table 1. Ligand concentration of the ConA coupled to PNIPAAm (PNIPAAm-ConA) was 11–14 mg/ml polymer and the binding capacity for β1,3-glucan was 2.7–4.9 mg/ml polymer. Desorption of β1,3-glucan from PNIPAAm-ConA complex released more than 50% of the conjugated amount from the first elution. For WGL coupled to PNIPAAm (PNIPAAm-WGL), ligand concentration was ca. 72 mg/ml polymer and the binding capacity for Ovomucoid was ca. 11.5 mg/ml polymer. The release rate from first elution of Ovomucoid resolved from PNIPAAm-WGL complex was more than 70% of the conjugated amount. Higher recovery rates can be obtained by repeating the desorption procedures.

Control

Binding Capacity of Commercially Available HiTrap ConA and HiTrap WGL

The data obtained from product instructions of commercially available immobilized lectins, HiTrap ConA and HiTrap WGL (HiTrap affinity columns: HiTrap ConA and HiTrap Wheat Germ Lectin, Amersham Biosciences Ltd. Piscataway, N.J., USA) is shown in Table 1.

TABLE 1

Binding capacity comparison between PNIPAAm-ConA and PNIPAAm-WGL of the present invention and HiTrap ConA and HiTrap WGL of commercially available immobilized lectins

|  | Control 1 | Example 3 |
| --- | --- | --- |
| Type of Ligand | Concanavalin A* | Concanavalin A |
| Ligand concentration | 12–18 mg/ml | 11–14 mg/ml |
| Binding capacity | 4 mg Transferrin/ml | 2.7–4.9 mg β-glucan/ml |
| First elution | NA** | >50% |
| Type of Ligand | Wheat Germ Lectin | Wheat Germ Lectin |
| Ligand concentration | 4.6–7.6 mg/ml | 72 mg/ml |
| Binding capacity | 4 mg Ovomucoid/ml | 11.5 mg Ovomucoid/ml |
| First elution | NA | >70% |

*Data obtained from Product instructions: HiTrap affinity columns, Hitrap ConA (1 ml) and HiTrap Wheat Germ Lectin (1 ml), Amersham Biosciences Ltd. Piscataway, NJ, USA)
**Not available The comparison of binding capacity and ligand concentration between the system of the present invention, PNIPAAm-ConA and PNIPAAm-WGL, as well as the commercially available immobilized lectins, HiTrap ConA and HiTrap WGL, is shown in Table 1. Regardless of the ligands, the binding capacity and ligand concentration of the system in the present invention is better than those of the commercialized system. In addition, desorption of β1,3-glucan from PNIPAAm-ConA complex with α-glucopyroside or α-mannopyroside as the competitive substrate released more than 50% of the conjugated amount from the first elution. The recovery rate from first elution of Ovomucoid resolved from PNIPPAm-WGL complex was more than 70% of the conjugated amount. Higher recovery rates can be obtained by repeating the desorption procedures.

The efficiency of the separation method of the present invention improves on the prior art. One advantage of the present invention is technical ease of purification. Use of Hi-Trap affinity columns lends itself to possible clogging or slow flow rates. Other advantages of the present invention include cost effectiveness, ease in synthesis of the polymer-affinity ligand conjugate and possibility for scale-up applications. The synthesis procedure allows for flexibility in conjugating a variety of affinity ligands to meet different needs. For example, IDA (iminodiacetate) can be conjugated to the PNIPAAm for the purification of poly-histidine tagged recombinant proteins. Also, polynucleotide thymine "groups" (poly T) can be the affinity ligand for purification of mRNA from total RNA.

While the invention has been particularly shown and described with the reference to the preferred embodiments thereof, it will be understood by those skilled in the art that various changes in form and details may be made without departing from the spirit and scope of the invention.

What is claimed is:

1. A method for the separation of a polysaccharide, comprising:
    (a) conjugating a ligand and a thermo-sensitive polymer to form a conjugate, wherein the ligand specifically recognizes a polysaccharide and the thermo-sensitive polymer features a lower critical solution temperature (LCST);
    (b) contacting the conjugate with a mixture containing the desired polysaccharide at a temperature lower than the LCST to specifically bind the conjugate with the polysaccharide via the ligand;
    (c) collecting the polysaccharide specifically bound to the conjugate at a temperature higher than the LCST; and
    (d) releasing the polysaccharide from the polysaccharide specifically bound conjugate.

2. The method as claimed in claim 1, wherein the thermo-sensitive polymer comprises poly(N-isopropylacrylamide), or poly(vinylmethylether), poly(vinylmethyloxazolidone).

3. The method as claimed in claim 2, wherein the thermo-sensitive polymer is poly(N-isopropylacrylamide).

4. The method as claimed in claim 1, wherein the ligand comprises lectins.

5. The method as claimed in claim 4, wherein the lectins comprise concanavalin A, lentil lectin, wheat germ lectin.

6. The method as claimed in claim 5, wherein the lectin is concanavalin A or wheat germ lectin.

7. The method as claimed in claim 1, wherein the mixture containing a desired polysaccharide is from plants or fungi.

8. The method as claimed in claim 7, wherein the fungi comprise *Ganoderma lucidum, Cordyceps sinensis*, or saccharomycetes.

9. The method as claimed in claim 7, wherein the plants comprise *Bupleurum falcatum*.

10. The method as claimed in claim 1, wherein the polysaccharide comprises β-glucan.

11. The method as claimed in claim 7, wherein the polysaccharide comprises β-glucan.

12. The method as claimed in claim 1, wherein step (d) comprises replacing the ligand bound polysaccharide by a competitive substrate.

13. The method as claimed in claim 12, wherein the competitive substrate comprises α-glucopyroside, α-mannopyroside, N-acetylglutamine, or sodium borate.

14. The method as claimed in claim 1, further comprising after step (d), recovering the conjugate after releasing the polysaccharide at a temperature lower than the LCST.

15. The method as claimed in claim 14, further comprising step repeating steps (b) to (e) to obtain a polysaccharide with high production rate.

16. The method as claimed in claim 1, further comprising purification of the polysaccharide obtained in step (d).

17. The method as claimed in claim 16, wherein the purification step comprises ion exchange or gel filtration.

* * * * *